United States Patent [19]

Drent et al.

[11] Patent Number: 4,975,404
[45] Date of Patent: Dec. 4, 1990

[54] PROCESS FOR THE PRODUCTION OF METHANOL AND CATALYST COMPOSITION FOR SAID PROCESS

[75] Inventors: Eit Drent; Willem W. Jager; Swan T. Sie, all of Amsterdam, Netherlands

[73] Assignee: Shell Oil Company, Houston, Tex.

[21] Appl. No.: 442,264

[22] Filed: Nov. 28, 1989

Related U.S. Application Data

[62] Division of Ser. No. 213,818, Jun. 30, 1988, Pat. No. 4,194,136.

[30] Foreign Application Priority Data

Nov. 19, 1987 [GB] United Kingdom ............... 8727058

[51] Int. Cl.$^5$ .............................................. B01J 31/04
[52] U.S. Cl. .................................... 502/170; 502/171
[58] Field of Search ............................... 502/170, 171

[56] References Cited

U.S. PATENT DOCUMENTS

| | | | |
|---|---|---|---|
| 3,422,081 | 1/1969 | Wexler et al. | 502/170 |
| 3,862,993 | 1/1975 | Yates et al. | 502/171 |
| 4,731,386 | 3/1988 | Onsager | 502/171 |
| 4,868,221 | 9/1989 | Sie et al. | 502/170 |

FOREIGN PATENT DOCUMENTS 0169634 12/1981 Japan.

*Primary Examiner*—Patrick P. Garvin
*Assistant Examiner*—E. D. Irzinski
*Attorney, Agent, or Firm*—Ronald R. Reper

[57] ABSTRACT

A process for the production of methanol comprising contacting a gaseous mixture of carbon monoxide and hydrogen with a catalytic system, obtainable by combination of:

component (a): a substantially dry nickel formate,
component (b): water in a predetermined amount in relation to the nickel formate amount and,
component (c): an alcoholate derived from an alkali metal or from an alkaline earth metal, and activation the combined components, and a catalyst system to be used in this process.

Preferably the molar ratio between nickel formate and water is in the rate from 1:3.5 to 1:1 and more preferably from 1:3.0 to 1:1.5.

4 Claims, 1 Drawing Sheet

$(H_2/CO)_I < (H_2/CO)_{II}$ $T_2 > T_1$

PROCESS FOR THE PRODUCTION OF METHANOL AND CATALYST COMPOSITION FOR SAID PROCESS

This is a division of application Ser. No. 213,818, filed June 30, 1988, now U.S. Pat. No. 4,194,136.

BACKGROUND OF THE INVENTION

The invention relates to a process for the production of methanol and a catalyst composition for said process.

More particularly the invention relates to a process for the production of methanol by reaction of carbon monoxide with hydrogen in the presence of a catalytic system in the liquid phase derived from at least a salt containing a cation of an element of group VIII of the Periodic Table of the Elements and an alcoholate.

A process for the production of methanol is described in specification U.S. Pat. No. 4,619,946 comprising reacting at relatively low temperature carbon monoxide with hydrogen in the presence of a catalytic system derived from sodium hydride, sodium alcoholate and acetate of nickel, palladium or cobalt. The alcoholate applied is preferably a lower alkanolate having 1-6 carbon atoms and more preferably a tert-alkanolate, while as metal salt nickel acetate is preferably used.

The catalyst is subjected to a conditioning or activating step for a prolonged time with a gaseous mixture comprising carbon monoxide and hydrogen at such an elevated temperature and elevated pressure that a substantial amount of carbon monoxide and hydrogen is consumed for this conditioning.

Also in specification U.S. Pat. No. 4,614,749 a process is disclosed for the production of methanol at relatively low temperature by reaction of carbon monoxide with hydrogen in the presence of a slurry catalyst system resulting from combination of
 a complex reducing agent comprising sodium hydride-alcohol and an acetate of nickel, palladium or cobalt, and
 a carbonyl complex of one of the group VI metals.

The alcohol to be applied is preferably selected from lower alkanols, having from 1 to 6 carbon atoms and more preferably tertiary amyl alcohol.

Another process for the production of methanol is described in published Japanese patent application No. 56-169,634. This process comprises reacting carbon monoxide and hydrogen in the presence of a catalyst comprising a nickel compound and a metal alkoxide, in the liquid phase at temperatures of 200° C. or lower. More preferably an alkali metal alkoxide might be used. The catalyst to be used for this process may be prepared by mixing a nickel compound with an alkali metal alkoxide, while it is preferable to use an organic diluent which is liquid under the preparation and use conditions of the catalyst system.

More particularly the teachings of this Japanese patent application instruct a person skilled in the art, that a high reaction rate may be reached by preparing the catalyst system with the use of a substantially alcohol free organic diluent and that it is desirable that an alcohol be not present in the reaction system at the commencement of the reaction.

Moreover from this Japanese patent application and especially from its example 2, it clearly appears that at low temperature only small amounts of methanol are produced in favour of production of methyl formate in large amounts.

Although improvements in the performances of the catalyst systems as described hereinbefore, could be reached as compared to those used in the conventional methanol manufacturing processes, requiring severe conditions, the still growing demand for cheaper methanol as starting material for a still increasing area of chemical syntheses evoked continuing research efforts for a further improved methanol manufacturing process as compared to the currently operated high pressure processes.

With the term improved methanol manufacturing process is meant a process utilizing a catalyst having enhanced activity at low temperatures, and retaining its activity for a long time under economically more attractive operating conditions.

An object of the present invention is therefore to provide such an improved manufacturing process for methanol. Another object of the present invention is to provide an improved catalyst system therefor.

SUMMARY OF THE INVENTION

As result of extensive research and experimentation such a process was now surprisingly found, which comprises contacting a gaseous mixture of carbon monoxide and hydrogen with a catalytic system, obtainable by combining the following components:
 component (a): a substantially dry nickel formate,
 component (b): water in a predetermined amount in relation to the nickel formate amount, and
 component (c): an alcoholate derived from an alkali metal or from an alkaline earth metal.

DESCRIPTION OF PREFERRED EMBODIMENTS

Figure 1:
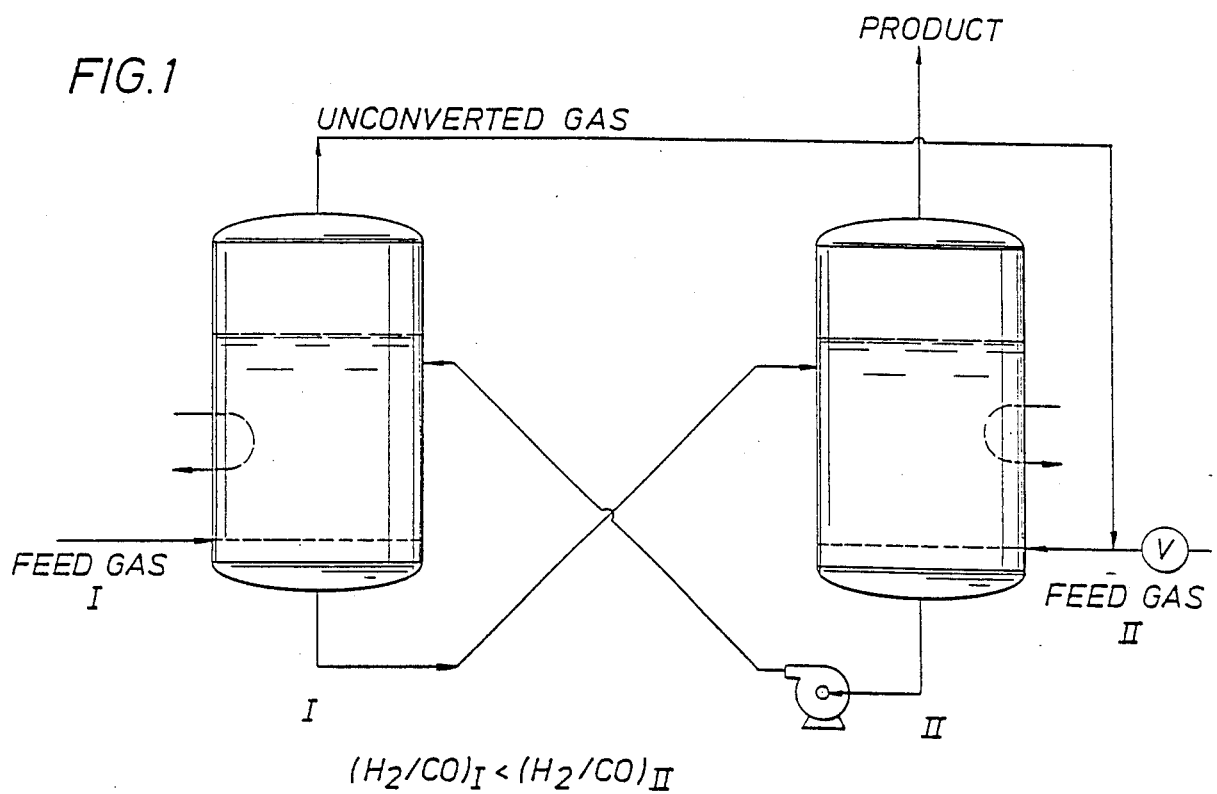
FIG. 1 schematically represents reaction equipment for carrying out a preferred embodiment of the invention.

With the term "substantially dry nickel formate" as used throughout the specification is meant nickel formate, which has a water content $\leq 0.3\%$ by weight.

Such nickel formate can be obtained by e.g. drying the starting salt in a vacuum oven at a temperature in the range of from 100°–200° C. and more preferably in the range of from 125°–175° C.

The water as component (b) may form in situ a predetermined, suitably selected amount of alcohol under activation and/or reaction conditions of the methanol synthesis.

The predetermined amount of water has been found to be at least 1.0 moles and at most 3.5 moles per mole nickel formate, for attractive yields of methanol, and will be more preferably in the range of from 1.5 to 3.0 mol water per mol nickel formate.

The process according to the present invention has surprisingly been found to be performed with optimal results at temperatures in the range of from 30°–100° C. and more preferably in the range of from 50°–90° C.

The pressure applied during the present process is not very critical and may vary within wide ranges, but preferably in the range of from 5 to 100 bar.

It will be appreciated that these attractive yields of methanol, which may be obtained by the hereinbefore defined catalytic system, operated at relative low temperature, could certainly not be predicted or even expected by persons skilled in the art and more particularly not on account of the Japanese patent application No. 56-169,634, which only taught that at low temperatures only small amounts of methanol could be produced and actually led away from the present process.

The alcoholate of component (c) is preferably a sodium alcoholate or a potassium alcoholate. Among the alcoholates preference is given to alkoxides, particularly to those having in the range of from 1 to 20 carbon atoms per molecule, such as sodium methoxide, sodium ethoxide, sodium propoxide, sodium butoxide, sodium isobutoxide, sodium ter-pentoxide and potassium-2-methyldodec-2-oxide. Most preferred is potassium tert-butoxide.

The process according to the present invention is carried out with preferably a substantially dry organic diluent in which the catalytic system is dissolved or is suspended. The substantially dry solvents may be obtained by methods known per se and preferably by drying over molecular sieves e.g. of the type 3A. However it will be appreciated that solvents may be used containing a minor content of water, which has to be compensated by the addition of a smaller predetermined amount. Suitably, a weight ratio of organic diluent to component (a) in the range of from 0.1 to 5000 is used, but this weight ratio may be lower than 0.1 or higher than 5000.

Examples of suitable diluents are ethers such as anisole, 2,5,8-trioxanonane (also referred to as "diglyme"), diethyl ether, diphenyl ether, diisopropyl ether and tetrahydrofuran; aromatic hydrocarbons, such as benzene, toluene, the three xylenes and ethylbenzene; halogenated aromatic compounds, such as chlorobenzene and o-dichlorobenzene; halogenated alkanes, such as dichloromethane and carbontetrachloride; alkanes, such as hexane, heptane, octane, 2,2,3-trimethylpentane and kerosene fractions; cycloalkanes, such as cyclohexane and methylcyclohexane; sulphones, such as diisopropyl sulphone, tetrahydrothiophene 1,1-dioxide (also referred to as "sulfolane"), 2-methyl-4-butylsulfolane and 3-methylsulfolane. Mixture of two or more solvents may be used. Very good results have been obtained with ethers and the use of diglyme is most preferred. The process may be carried out using a molar ratio of component (a) to component (b) which is not critical and may vary within wide ranges, preferably in the range of from 1:0.2 to 1:20 and more preferably of from 1:3 to 1:8.

The carbon monoxide and hydrogen may be used as pure gases or diluted with an inert gas such as a noble gas or nitrogen. The process according to the present invention may be carried out using a molar ratio carbon monoxide to hydrogen in the gaseous mixture which is not critical and may vary within wide ranges, suitably in the range of from 1:0.2 to 1:20. The carbon monoxide and hydrogen may preferably be obtained by partial oxidation of hydrocarbons, for example of natural gas with air or coal gasification, resulting in carbon monoxide-hydrogen mixtures containing nitrogen.

The methanol produced according to the invention forms another feature of the invention. It may be used for a variety of purposes, for example for the manufacture of synthetic gasoline, as a fuel component and for the production of methyl tert-butyl ether.

The process according to the present invention may be carried out batchwise, semi-continuously or continuously.

It is preferred to remove methanol in the gaseous phase from the reaction mixture. This can be done by stripping the reaction mixture with carbon monoxide and hydrogen. Methanol can be recovered from the used stripping gas in any suitable manner for example by condensation.

It will be appreciated that another object of the present invention is formed by the catalyst systems in the process as described hereinbefore and which may be obtained by combining the following components:
  component (a): a substantial dry nickel formate,
  component (b): a predetermined amount of water and more specifically an amount of from 1.5 to 3.5 equivalents per equivalent nickel, and
  component (c): an alcoholate derived from an alkali metal or from an alkaline earth metal.

Most preferably the catalyst systems will include from 2.0 to 3.0 mol water per mol nickel formate.

It will be appreciated that another object of the invention is formed by the before identified catalyst systems, mixed with one or more inert diluents and or carbon monoxide and hydrogen under an operational pressure suitable for the process of the invention, or lower.

It will be appreciated that according to a more preferred embodiment of the process of the present invention, it may be carried out as a two step process in at least two separated reactor zones, in which two different synthesis gas streams are introduced, containing excess carbon monoxide and excess hydrogen respectively ($H_2/CO$ ratio varying from 0.5 to 1.9 and more preferably 1.0–1.8 and $H_2/CO$ ratio varying from 2.5 to 4.5 and more preferably from 2.9 to 3.5) compared to the stoichiometric consumption ratio ($H_2/CO=2$).

In one of the zones a formate ester is formed (carbonylation step) e.g. methyl formate in the liquid phase using the catalyst system of the present invention in a low temperature process and using a feed gas, which is relatively rich in carbon monoxide, while in the other reaction zone this formate is hydrogenated in the liquid phase using the same catalyst composition and using a feed gas, which is relatively rich in hydrogen. The catalyst solution or slurry is circulated between the two reaction vessels.

In case a single synthesis gas stream is to be converted to methanol, a synthesis gas stream of higher $H_2/CO$ ratio is obtained by partial conversion of the first mentioned stream to form mainly the formate ester. The unconverted, hydrogen enriched residual gas stream from the first zone may be used to hydrogenate this formate ester in the second zone.

According to a more preferred embodiment these two feed streams are derived from natural gas, which is converted by partial oxidation to synthesis gas, relatively rich in carbon monoxide, and by steam reforming to a gas relatively rich in hydrogen.

Although it might initially seem advantageous to carry out the two consecutive reaction steps, i.e.,
  (a) reaction of a carbon monoxide containing gas with an alcoholate to form a formate ester, e.g. methyl formate from alkali methanolate,
  (b) hydrogenation/hydrogenolysis of the formate ester to form methanol and the alcohol from the original alcoholate (preferably also methanol),
in a single reactor being the most simple and straight forward way, the following negative features of such single step process may be appreciated:

(1) Formation of formate is a rapid reaction, but is limited by thermodynamic equilibrium, while hydrogenation of formate on the other hand is only limited by kinetics. Although the equilibrium limitation of alcohol carbonylation was found to be lifted by consecutive removal of formate, the steady state formate concentration has appeared to be relatively low since the conditions are governed to a large extent by the requirements of the second step.

(2) When a stoichiometric hydrogen/carbon monoxide synthesis gas mixture is converted at high methanol yield, the methanol concentration in the liquid catalyst phase will be found to be relatively high under steady state conditions, even when originally a catalyst with a higher alcohol and/or alcoholate component has been applied.

It has been found now, that methanol is a less suitable alcohol component than an optimally selected one as far as the reaction is concerned with reference to reaction rates, mass transfer, gas solubilisation etc.

Moreover, at high methanol concentrations methylformate will inevitably be formed in competition with other formates.

Since methylformate is relatively volatile, it will be a substantial by-product of the methanol produced unless the steady state formate concentration can be kept deliberately low, which is not inducive to a high hydrogenation rate. Possible methylformate as byproduct can be reconverted into methanol.

The hereinbefore described embodiment may be more particularly be carried out in a reaction equipment according to the FIG. 1.

One of the individually produced gas mixtures relatively rich in CO is introduced in the left reactor where carbonylation is the predominant reaction. The carbonylation rate as well as equilibrium are favoured by the relatively high CO partial pressure (i.e. more than in a stoichiometric mixture usually applied).

The ester hydrogenation step (b) may predominantly take place in the right hand reactor. Herein the reaction rate benefits from the high hydrogen partial pressure and the relatively low CO pressure.

At a substantial conversion of the low $H_2/CO$ gas in the left reactor, there will be a net formate production with a $H_2/CO$ consumption ratio less than 2. In the right reactor, substantial conversion of the high $H_2/CO$ gas implies a net consumption of formate. Formate production and consumption may accurately balanced by control of the circulation of liquid catalyst system.

Figure 2:
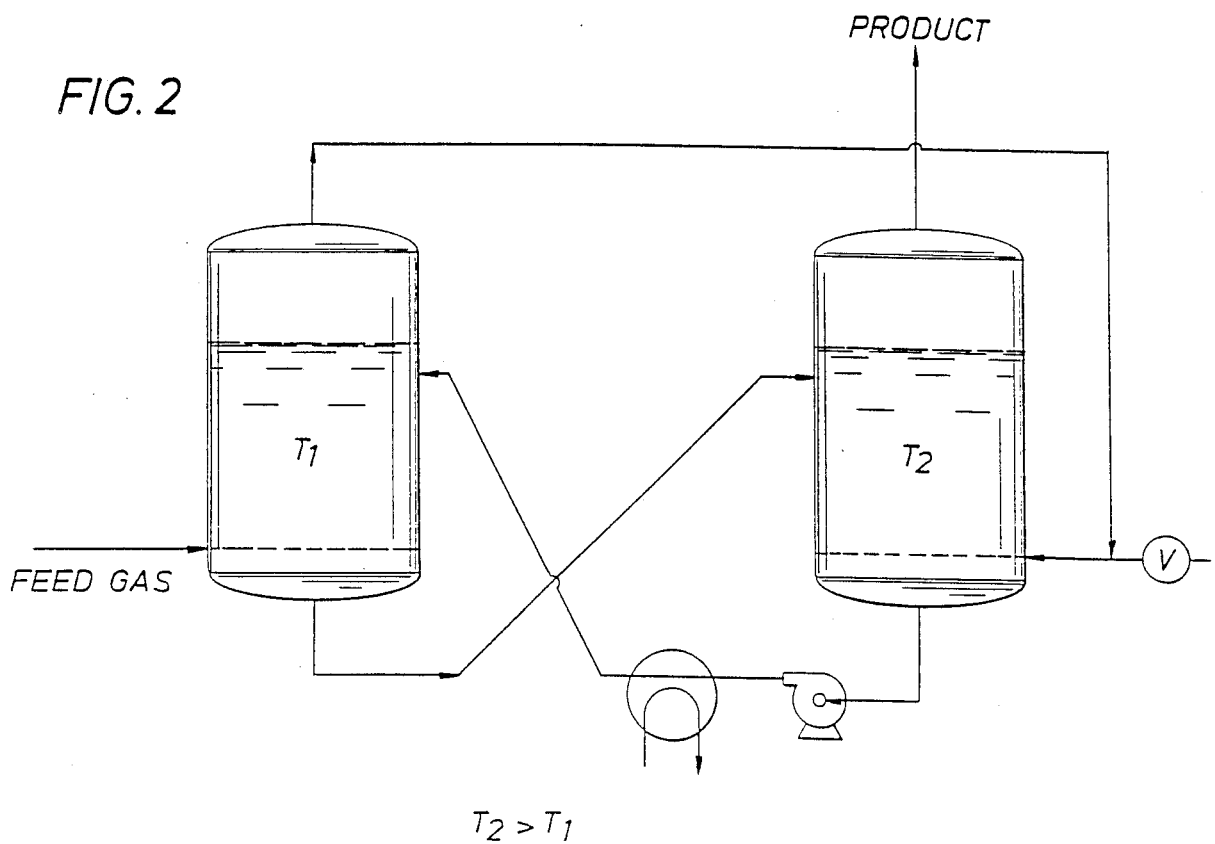
FIG. 2 schematically represents reaction equipment for carrying out another preferred embodiment of the invention.

According to a more preferred embodiment the carbonylation reaction step is carried out at relatively low temperature (from 30°–70° C.) in the left reactor, taking into account that this reaction step is a fast but equilibrium limited reaction, while the second hydrogenation reaction step is carried out at relatively higher temperature (from 70°–120° C.) in the right hand reactor (reference is made to the FIG. 2), taking into account that the ester hydrogenation is not limited by equilibrium but by kinetics. Such a temperature difference as indicated hereinbefore, will be reached automatically, if the total reaction heat is removed from the circulating liquid catalyst system.

It will be appreciated that the before described embodiment offers a greater degree of flexibility than a single stage process, which leads to an overall better performance, e.g. a lower total reactor volume, while also the problem of methanol build up and byproduct methyl formate will be minimized.

Moreover, this embodiment can certainly not be regarded as obvious to a skilled person who might only be inclined to look for improved single stage processes, due to the general conception that separate reaction vessels would mean a disadvantage.

The following example further illustrate the invention, without however restricting the scope thereof to these particular embodiments.

All experiments were carried out in a 300 ml magnetically stirred Hastelloy C (Hastelloy is a trade name) autoclave. The reaction mixtures obtained were analyzed by means of gas-liquid chromatography.

Nickel formate was used which had been preheated under vacuum at 150° C. during 16 hours.

EXAMPLE

The autoclave was charged under a nitrogen atmosphere with diglyme (50 ml), substantially dry nickel formate (10 mmol) and 20 mmol water, and heated to a temperature of 45° C. under stirring and kept this temperature for 0.5 h. Then a solution of 60 mmol potassium tert.butylate in 50 ml diglyme was added. The autoclave was sealed and a mixture of carbon monoxide and hydrogen was introduced into the autoclave until a partial CO pressure of 15 bar and a partial $H_2$ pressure of 30 bar was reached.

The autoclave was further heated to a temperature of 80° C. and kept 2 hours at this temperature and 3 hours at 100° C. The pressure was kept at a value between 30 and 60 bar by intermittent introduction of additional carbon monoxide and hydrogen in a ratio of 1:3.

After termination of the reaction, 6.1 g methanol and 1.8 g methyl formate had been obtained.

COMPARATIVE EXAMPLE a

In about the same way as described under example 1, an experiment was carried out, with the difference that instead of 20 mmol water 40 mmol were added.

The pressure was kept in the range from 30–60 bar by continue addition of hydrogen and carbon monoxide in a 3:1 ratio.

After a reaction time of 2 hours at 80° C. and 3 hours at 100° C. 0.7 g of methanol could be detected.

COMPARATIVE EXAMPLE b

In about the same way as described under example 1, an experiment was carried out, with the difference that no water was added.

The pressure was kept in the range from 30–60 bar by continue addition of hydrogen and carbon monoxide in a 3:1 ratio.

After a reaction time of 2 hours at 80° C. and 3 hours at 100° C. an only small amount of methanol (1.5 g) had been obtained.

What is claimed is:

1. A catalyst system for the production of methanol obtained by combination of:
component (a): a substantially dry nickel formate,
component (b): water in a molar ratio of water to nickel formate in the range from 1:1 to 1:3.5, and amount of nickel formate, and
component (c): an alcoholate derived from an alkali metal or from an alkaline earth metal.

2. A catalyst system according to claim 1, wherein component (c) is potassium tert-butoxide.

3. A catalyst system according to claim 1, characterized in that the molar ratio of component (b) to component (a) is in the range of from 1.5 to 3:1.

4. A catalyst system according to claim 1 mixed with an organic diluent in a weight ratio of diluent to component (a) in the range of from 0.1 to 5000.

* * * * *